(12) United States Patent
Silvestri et al.

(10) Patent No.: US 12,415,024 B2
(45) Date of Patent: *Sep. 16, 2025

(54) DUAL CHAMBER BLOOD RESERVOIR

(71) Applicant: Sorin Group Italia S.r.l., Milan (IT)

(72) Inventors: Claudio Silvestri, Quarantoli Mirandola (IT); Gabriele Tommasi, Cavezzo (IT)

(73) Assignee: Sorin Group Italia S.r.l., Milan (IT)

( * ) Notice: Subject to any disclaimer, the term of this patent is extended or adjusted under 35 U.S.C. 154(b) by 588 days.

This patent is subject to a terminal disclaimer.

(21) Appl. No.: 17/859,699

(22) Filed: Jul. 7, 2022

(65) Prior Publication Data

US 2022/0339335 A1 Oct. 27, 2022

Related U.S. Application Data

(60) Continuation of application No. 16/273,459, filed on Feb. 12, 2019, now Pat. No. 11,389,580, which is a
(Continued)

(30) Foreign Application Priority Data

Jul. 12, 2011 (EP) .................................. 11173655

(51) Int. Cl.
*A61M 1/36* (2006.01)
*A61M 1/16* (2006.01)

(52) U.S. Cl.
CPC ........ *A61M 1/3627* (2013.01); *A61M 1/1698* (2013.01); *A61M 1/3632* (2014.02);
(Continued)

(58) Field of Classification Search
CPC .............. A61M 1/3627; A61M 1/3632; A61M 1/1698; A61M 1/3666; A61M 1/3638
See application file for complete search history.

(56) References Cited

U.S. PATENT DOCUMENTS 3,551,072 A 12/1970 Zemmerly
3,588,589 A 6/1971 Vonk
(Continued)

FOREIGN PATENT DOCUMENTS

CN 86103696 A 1/1987
CN 1147964 A 4/1997
(Continued)

OTHER PUBLICATIONS

Catalog of Products, Terumo Europe Cardiovascular Systems, 142 pages, 2009.
(Continued)

*Primary Examiner* — Ariana Zimbouski
(74) *Attorney, Agent, or Firm* — Seager, Tufte & Wickhem LLP (57) ABSTRACT

A blood reservoir may be used in combination with other elements such as a heart lung machine (HLM), oxygenator, heat exchanger, arterial filter and the like to form an extracorporeal blood circuit that may be employed in a procedure such as a bypass procedure. The blood reservoir may be configured to receive, filter and store blood from a number of sources including vent blood (from within the heart), venous blood (from a major vein), purge blood (from a sampling line) and cardiotomy or suction blood (from the surgical field).

19 Claims, 10 Drawing Sheets

Related U.S. Application Data continuation of application No. 14/668,933, filed on Mar. 25, 2015, now Pat. No. 10,213,541, which is a division of application No. 13/181,688, filed on Jul. 13, 2011, now Pat. No. 9,011,769.

(52) U.S. Cl.
CPC ........ *A61M 1/3638* (2014.02); *A61M 1/3666* (2013.01); *A61M 2202/0413* (2013.01); *A61M 2205/75* (2013.01)

(56) References Cited

U.S. PATENT DOCUMENTS

| | | |
|---|---|---|
| 3,588,859 A | 6/1971 | Petree |
| 3,851,181 A | 11/1974 | Heule |
| 3,927,980 A | 12/1975 | Leonard |
| 4,006,745 A | 2/1977 | Sorenson et al. |
| 4,170,765 A | 10/1979 | Austin et al. |
| 4,177,649 A | 12/1979 | Venema |
| 4,193,004 A | 3/1980 | Lobdell et al. |
| 4,275,726 A | 6/1981 | Schael |
| 4,309,871 A | 1/1982 | Venema |
| 4,374,088 A | 2/1983 | Stenberg et al. |
| 4,464,164 A | 8/1984 | Troutner et al. |
| 4,466,804 A | 8/1984 | Hino |
| 4,490,331 A | 12/1984 | Steg, Jr. |
| 4,518,318 A | 5/1985 | Jensen et al. |
| 4,530,696 A | 7/1985 | Bisera et al. |
| 4,599,093 A | 7/1986 | Steg, Jr. |
| 4,602,344 A | 7/1986 | Ferretti et al. |
| 4,642,089 A | 2/1987 | Zupkas et al. |
| 4,664,682 A | 5/1987 | Monzen |
| 4,678,404 A | 7/1987 | Lorett et al. |
| 4,701,101 A | 10/1987 | Sapoff |
| 4,705,497 A | 11/1987 | Shitaokoshi et al. |
| 4,782,451 A | 11/1988 | Mazzarella et al. |
| 4,828,543 A | 5/1989 | Weiss et al. |
| 4,846,800 A | 7/1989 | Ouriel et al. |
| 4,876,066 A | 10/1989 | Bringham et al. |
| 4,955,874 A | 9/1990 | Farrar et al. |
| 4,984,462 A | 1/1991 | Hass, Jr. et al. |
| 4,991,433 A | 2/1991 | Warnaka et al. |
| 5,039,430 A | 8/1991 | Corey, Jr. |
| 5,039,482 A | 8/1991 | Panzani et al. |
| 5,043,707 A | 8/1991 | Heinze |
| 5,049,146 A | 9/1991 | Bringham et al. |
| 5,055,198 A | 10/1991 | Shettigar |
| 5,060,512 A | 10/1991 | Kanashige et al. |
| 5,061,236 A | 10/1991 | Sutherland et al. |
| 5,078,677 A | 1/1992 | Gentelia et al. |
| 5,110,549 A | 5/1992 | Gordon |
| 5,112,480 A | 5/1992 | Hukasawa |
| 5,120,303 A | 6/1992 | Hombrouckx |
| 5,135,485 A | 8/1992 | Cohen et al. |
| 5,147,187 A | 9/1992 | Ito et al. |
| 5,149,318 A | 9/1992 | Lindsay |
| 5,158,533 A * | 10/1992 | Strauss ............... A61M 1/3627 210/489 |
| 5,178,603 A | 1/1993 | Prince |
| 5,186,431 A | 2/1993 | Tamari |
| 5,215,519 A | 6/1993 | Shettigar |
| 5,226,265 A | 7/1993 | Kelly et al. |
| 5,240,380 A | 8/1993 | Mabe |
| 5,266,265 A | 11/1993 | Raible |
| 5,270,005 A | 12/1993 | Raible |
| 5,282,783 A | 2/1994 | Lindsay |
| 5,303,585 A | 4/1994 | Lichte |
| 5,304,164 A | 4/1994 | Lindsay |
| 5,318,510 A | 6/1994 | Cathcart |
| 5,399,074 A | 3/1995 | Nose et al. |
| 5,403,273 A | 4/1995 | Lindsay |
| 5,411,705 A | 5/1995 | Thor et al. |
| 5,458,566 A | 10/1995 | Herrig et al. |
| 5,458,567 A | 10/1995 | Cathcart |
| 5,458,579 A | 10/1995 | Chodorow et al. |
| 5,563,490 A | 10/1996 | Kawaguchi et al. |
| 5,563,584 A | 10/1996 | Rader et al. |
| 5,586,085 A | 12/1996 | Lichte |
| 5,591,399 A | 1/1997 | Goldman et al. |
| 5,604,315 A | 2/1997 | Briefer et al. |
| 5,619,993 A | 4/1997 | Lee |
| 5,667,485 A | 9/1997 | Lindsay |
| 5,725,357 A | 3/1998 | Nakazeki et al. |
| 5,756,940 A | 5/1998 | Van Driel et al. |
| 5,770,073 A | 6/1998 | Bach et al. |
| 5,775,879 A | 7/1998 | Durando |
| 5,800,721 A | 9/1998 | McBride |
| 5,823,045 A | 10/1998 | Van Driel et al. |
| 5,826,576 A | 10/1998 | West |
| 5,849,186 A * | 12/1998 | Raneri ............... A61M 1/3623 210/489 |
| 5,928,180 A | 7/1999 | Krivitski et al. |
| 5,955,672 A | 9/1999 | Van Driel et al. |
| 6,017,493 A | 1/2000 | Cambron et al. |
| 6,048,363 A | 4/2000 | Nagyszalanczy et al. |
| 6,123,519 A | 9/2000 | Kato et al. |
| 6,146,411 A | 11/2000 | Noda et al. |
| 6,164,325 A | 12/2000 | Braun |
| 6,287,270 B1 | 9/2001 | Fini |
| 6,337,049 B1 | 1/2002 | Tamari |
| 6,345,214 B1 | 2/2002 | Dulphy-Vigor et al. |
| 6,475,176 B2 | 11/2002 | Fini |
| 6,542,848 B1 | 4/2003 | Neeser et al. |
| 6,562,012 B1 | 5/2003 | Brown et al. |
| 6,564,627 B1 | 5/2003 | Sabini et al. |
| 6,592,340 B1 | 7/2003 | Horo et al. |
| 6,631,639 B1 | 10/2003 | Dam et al. |
| 6,652,495 B1 | 11/2003 | Walker |
| 6,694,570 B2 | 2/2004 | Chen |
| 6,770,048 B2 | 8/2004 | Fini |
| 6,931,926 B1 | 8/2005 | Van Ee |
| 7,072,769 B2 | 7/2006 | Fletcher-Haynes et al. |
| 7,147,614 B2 | 12/2006 | Fini |
| 7,591,812 B1 | 9/2009 | Tamari |
| 7,694,570 B1 | 4/2010 | Dam et al. |
| 7,982,612 B2 | 7/2011 | Braun |
| 8,105,265 B2 | 1/2012 | Demers et al. |
| 8,394,321 B2 | 3/2013 | Franzoni et al. |
| 8,409,124 B2 | 4/2013 | Steffens et al. |
| 8,500,673 B2 | 8/2013 | Zanotti et al. |
| 8,506,513 B2 | 8/2013 | Rossi et al. |
| 8,734,376 B2 | 5/2014 | Simpson et al. |
| 9,011,769 B2 * | 4/2015 | Silvestri ............... A61M 1/3638 604/6.14 |
| 10,213,541 B2 * | 2/2019 | Silvestri ............... A61M 1/3666 |
| 10,458,833 B2 | 10/2019 | Rossi |
| 11,389,580 B2 * | 7/2022 | Silvestri ............... A61M 1/3666 |
| 2001/0013822 A1 | 8/2001 | Nazarian et al. |
| 2001/0050256 A1 | 12/2001 | Krivitski |
| 2002/0032399 A1 | 3/2002 | Fini |
| 2002/0033181 A1 | 3/2002 | Groth et al. |
| 2002/0038392 A1 | 3/2002 | De La Huerga |
| 2002/0085952 A1 | 7/2002 | Ellingboe et al. |
| 2002/0094300 A1 * | 7/2002 | Yokoyama ............ A61M 1/3627 604/406 |
| 2002/0128582 A1 | 9/2002 | Farrell et al. |
| 2002/0133066 A1 | 9/2002 | Miller et al. |
| 2003/0033871 A1 | 2/2003 | Carroll et al. |
| 2003/0035730 A1 | 2/2003 | Schob |
| 2003/0045772 A1 | 3/2003 | Reich et al. |
| 2003/0139643 A1 | 7/2003 | Smith et al. |
| 2003/0144646 A1 | 7/2003 | Se et al. |
| 2003/0175151 A1 | 9/2003 | Ghelli et al. |
| 2004/0047737 A1 | 3/2004 | Nose et al. |
| 2004/0064292 A1 | 4/2004 | Beck et al. |
| 2004/0152944 A1 | 8/2004 | Medvedev et al. |
| 2005/0025630 A1 | 2/2005 | Ayre et al. |
| 2005/0119600 A1 | 6/2005 | Lucke et al. |
| 2005/0230313 A1 | 10/2005 | O'Mahony et al. |
| 2006/0015056 A1 | 1/2006 | Ellingboe et al. |
| 2006/0089695 A1 | 4/2006 | Bolea et al. |
| 2006/0092360 A1 | 5/2006 | Hong |
| 2006/0150596 A1 | 7/2006 | Takahashi et al. |

(56) References Cited

U.S. PATENT DOCUMENTS

| | | |
|---|---|---|
| 2006/0167400 A1 | 7/2006 | Ellingboe et al. |
| 2006/0226087 A1 | 10/2006 | Robinson et al. |
| 2006/0260392 A1 | 11/2006 | Hedrick |
| 2006/0277269 A1 | 12/2006 | Dent et al. |
| 2007/0017518 A1 | 1/2007 | Farrugia et al. |
| 2007/0110612 A1 | 5/2007 | Ito |
| 2007/0142923 A1 | 6/2007 | Ayre et al. |
| 2007/0194981 A1 | 8/2007 | Hagg et al. |
| 2007/0209662 A1 | 9/2007 | Bowen et al. |
| 2008/0027368 A1 | 1/2008 | Kollar et al. |
| 2008/0078382 A1 | 4/2008 | LeMahieu et al. |
| 2008/0171960 A1 | 7/2008 | Brieske et al. |
| 2008/0245530 A1 | 10/2008 | Kuzmichev |
| 2008/0275377 A1 | 11/2008 | Paolini et al. |
| 2009/0012443 A1 | 1/2009 | Ghelli et al. |
| 2009/0099498 A1 | 4/2009 | Demers et al. |
| 2009/0149950 A1 | 6/2009 | Wampler |
| 2010/0042038 A1 | 2/2010 | Urdahl et al. |
| 2010/0140182 A1 | 6/2010 | Chapman et al. |
| 2010/0275953 A1 | 11/2010 | Orue et al. |
| 2010/0280430 A1 | 11/2010 | Caleffi et al. |
| 2011/0098625 A1 | 4/2011 | Masala et al. |
| 2011/0257576 A1 | 10/2011 | Simpson et al. |
| 2011/0257578 A1 | 10/2011 | Zanotti et al. |
| 2011/0257579 A1 | 10/2011 | Rossi et al. |
| 2012/0067133 A1 | 3/2012 | Waldrop et al. |
| 2012/0130299 A1 | 5/2012 | Knott et al. |
| 2012/0226446 A1 | 9/2012 | Nelson et al. |
| 2013/0017119 A1 | 1/2013 | Silvestri et al. |
| 2013/0303965 A1 | 11/2013 | Rossi et al. |
| 2013/0331758 A1 | 12/2013 | Meibaum et al. |
| 2014/0278156 A1 | 9/2014 | Thompson et al. |
| 2015/0100253 A1 | 4/2015 | Austerlitz et al. |
| 2015/0196703 A1 | 7/2015 | Silvestri et al. |
| 2015/0367120 A1 | 12/2015 | Kusters et al. |
| 2017/0089746 A1 | 3/2017 | Rossi |
| 2019/0070353 A1 | 3/2019 | Knott et al. |

FOREIGN PATENT DOCUMENTS

| | | |
|---|---|---|
| CN | 1197677 A | 11/1998 |
| CN | 1458851 A | 11/2003 |
| DE | 2455229 A1 | 5/1976 |
| DE | 2754894 A1 | 6/1979 |
| DE | 3935502 A1 | 5/1991 |
| DE | 19840399 A1 | 3/1999 |
| DE | 102004040441 A1 | 6/2006 |
| DE | 102005001779 A1 | 9/2006 |
| DE | 102005029682 A1 | 12/2006 |
| DE | 102007026010 B4 | 11/2010 |
| EP | 0371173 A1 | 6/1990 |
| EP | 0587251 A1 | 3/1994 |
| EP | 0472480 B1 | 8/1995 |
| EP | 0820775 A2 | 1/1998 |
| EP | 0952433 A1 | 10/1999 |
| EP | 1053760 A2 | 11/2000 |
| EP | 1070509 A2 | 1/2001 |
| EP | 0690730 B1 | 5/2002 |
| EP | 1210956 A2 | 6/2002 |
| EP | 1003575 B1 | 10/2004 |
| EP | 0766974 B1 | 9/2006 |
| EP | 2754458 A2 | 7/2014 |
| EP | 2435106 B1 | 11/2014 |
| EP | 2842584 A1 | 3/2015 |
| FR | 2811752 A1 | 1/2002 |
| GB | 2009862 A | 6/1979 |
| GB | 2109934 A | 6/1983 |
| JP | S5623960 A | 3/1981 |
| JP | S57500411 A | 3/1982 |
| JP | S62258671 A | 11/1987 |
| JP | H0391352 U | 9/1991 |
| JP | H0819602 A | 1/1996 |
| JP | H08506982 A | 7/1996 |
| JP | H11506701 A | 6/1999 |
| JP | 2944749 B2 | 9/1999 |
| JP | 20000000299 A | 1/2000 |
| JP | 2001503665 A | 3/2001 |
| JP | 2001165878 A | 6/2001 |
| JP | 2001204815 A | 7/2001 |
| JP | 2001514939 A | 9/2001 |
| JP | 2001523339 A | 11/2001 |
| JP | 200233648 A | 11/2002 |
| JP | 2003052717 A | 2/2003 |
| JP | 2003126246 A | 5/2003 |
| JP | 2005066013 A | 3/2005 |
| JP | 2006025531 A | 1/2006 |
| JP | 2006325750 A | 12/2006 |
| JP | 2007130290 A | 5/2007 |
| JP | 2008000597 A | 1/2008 |
| JP | 2008194386 A | 8/2008 |
| JP | 2008270595 A | 11/2008 |
| JP | 2009240428 A | 10/2009 |
| JP | 2009287593 A | 12/2009 |
| JP | 2011076394 A | 4/2011 |
| NO | 9965413 A1 | 12/1999 |
| WO | 9421311 A2 | 9/1994 |
| WO | 9624397 A2 | 8/1996 |
| WO | 9733672 A1 | 9/1997 |
| WO | 9820957 A1 | 5/1998 |
| WO | 9848868 A1 | 11/1998 |
| WO | 9908734 A1 | 2/1999 |
| WO | 0015154 A1 | 3/2000 |
| WO | 0044415 A1 | 8/2000 |
| WO | 0147442 A1 | 7/2001 |
| WO | 0176656 A2 | 10/2001 |
| WO | 0239931 A1 | 5/2002 |
| WO | 0239933 A1 | 5/2002 |
| WO | 02095675 A1 | 11/2002 |
| WO | 03026724 A1 | 4/2003 |
| WO | 2006021295 A1 | 3/2006 |
| WO | 2006057650 A2 | 6/2006 |
| WO | 2006122282 A2 | 11/2006 |
| WO | 2007018513 A1 | 2/2007 |
| WO | 2008119993 A1 | 10/2008 |
| WO | 2009144522 A1 | 12/2009 |
| WO | 2010041604 A1 | 4/2010 |
| WO | 2014041604 A1 | 3/2014 |

OTHER PUBLICATIONS

Definition of "Cylinder", downloaded from http://dictionary.reference.com/browse/cylinder, 3 pages, download on Apr. 28, 2014.

European Search Report and Search Opinion Received for EP Application No. 14164506.9, dated Sep. 19, 2014, 10 pages.

European Search Report issued in EP Application No. 11173655, completed Nov. 30, 2011, 9 pages.

Extended European Search Report issued in 14188440.3, dated Jan. 30, 2015, 7 pages.

Fischer, Betriebsmesstechnik, unveranderte Auflage, VEB Verlag Technik Berlin, 3 pages (machine translations: Business measuring technique, unchanged edition). 1986.

Henriksen et al; "Envisioning Patient Safety in the Year 2025: Eight Perspectives," Advances in Patient Safety: New Directions and Alternative Approaches, Agency for Healthcare Research and Quality, vol. 1, Aug. 2008.

International Preliminary Report on Patentability issued in PCT/IB2014/061491, dated Dec. 1, 2016, 12 pages.

International Preliminary Report on Patentability received for PCT Patent Application No. PCT/IB2011/051639, dated Nov. 1, 2012 10 pages.

International Preliminary Report on Patentability received for PCT Patent Application No. PCT/IB2012/053497, dated Jan. 23, 2014, 10 pages.

International Preliminary Report on Patentability, Chapter 11, issued in PCT/EP2010/055522, (with translation), dated May 31, 2013 13 pages.

International Search Report and Written Opinion issued in PCT/EP2010/055522, (with translation) dated Aug. 6, 2010, 10 pages.

International Search Report and Written Opinion issued in PCT/IB2011/051639, dated Nov. 18, 2011, 15 pages.

(56) References Cited

OTHER PUBLICATIONS

International Search Report and Written Opinion issued in PCT/IB2014/061491, dated Mar. 6, 2015, 16 pages.
International Search Report and Written Opinion received for PCT Patent Application No. PCT/IB2012/053497, dated Nov. 15, 2012. 12 pages.
Klonoff, Designing an Artificial Pancreas System to be Compatible with Other Medical Devices, Journal of Diabetes Science and Technology, vol. 2, No. 5, pp. 741-745, Sep. 2008.
Terumo Europe Cardiovascular Systems, Innovative Products for the Treatment of Cardiovascular Disease, 2006 Terumo Europe, 105 pages, 2006.
Van Der Togt et al, "Electromagnetic Interference from Radio Frequency Identification Inducing Potentially Hazardous Incidents in Critical Care Medical Equipment," JAMA, vol. 299, No. 24, 7 pages, Jun. 25, 2008.
Weber, "Talking Barcodes that Change our Lives," BBC News, 3 pages, Published Apr. 28, 2004. (check date).
Wikipedia, "Fullstandmeussing" [online]. Retrieved from https://de.wikipedia.org/w/index.php?title=F%C3%BCIIstandmessung&oldid=69-998631, last modified Jan. 30, 2010. English translation retrieved from https://en.wikipedia.org/wiki/Level_sensor, Oct. 18, 2016.
International Search and Written Opinion issued in PCT/IB2014/061491, dated Mar. 8, 2015, 16 pages.
International Preliminary Report on Patentability issued in PCT/EP2010/055444, dated Oct. 5, 2011, 10 pages (with English translation).
International Search Report and Written Opinion issued in PCT/EP2010/055444, dated Aug. 20, 2010, 10 pages (English Translation of SR).

\* cited by examiner

DUAL CHAMBER BLOOD RESERVOIR

CROSS REFERENCE TO RELATED APPLICATION

This application is a continuation of U.S. application Ser. No. 16/273,459 filed Feb. 12, 2019, which is a continuation of U.S. application Ser. No. 14/668,933 filed Mar. 25, 2015, now U.S. Pat. No. 10,213,541, which is a division of U.S. application Ser. No. 13/181,688, filed Jul. 13, 2011, now U.S. Pat. No. 9,011,769, which claims priority to European Patent Application 11173655.9, filed Jul. 12, 2011, all of which are hereby incorporated by reference in their entirety.

TECHNICAL FIELD

The present invention relates generally to blood reservoirs for oxygenators used in blood perfusion systems.

BACKGROUND

Blood perfusion involves encouraging blood through the vessels of the body. For such purposes, blood perfusion systems typically include the use of one or more pumps in an extracorporeal circuit that is interconnected with the vascular system of a patient. Many surgical procedures require or prefer temporary cessation of the heart to create a still operating field. Such procedures may thus rely upon a cardiopulmonary bypass (CPB) perfusion system that temporarily replaces the function of the heart and lungs. Examples of such procedures include the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs, respectively.

More specifically, in cardiopulmonary bypass procedures, oxygen-poor blood (i.e., venous blood) is gravity-drained or vacuum-suctioned from a large vein entering the heart or another major vein in the body (e.g., femoral) and is transferred through a venous line in the extracorporeal circuit. The venous blood is pumped to an oxygenator that provides for oxygen transfer to the blood. Oxygen may be introduced into the blood by, for example, transfer across a membrane. Concurrently, carbon dioxide is removed across the membrane. The oxygenated blood is filtered and then returned through an arterial line to the aorta, femoral, or other artery.

In many cases, an extracorporeal blood circuit includes a blood reservoir that can be used to collect, filter and de-aerate blood from a variety of different sources. For example, a blood reservoir may receive one or more of venous blood from a large vein, vent blood that is collected within the heart and cardiotomy or suction blood that is collected from outside the heart but within the surgical field.

SUMMARY

The present invention relates to a blood reservoir that may be used in combination with other elements such as a heart lung machine (HLM), oxygenator, heat exchanger, arterial filter and the like to form an extracorporeal blood circuit. The blood reservoir, as will be described in greater detail herein, may be configured to receive, filter and store blood from a number of sources including vent blood (from within the heart), venous blood (from a major vein), purge blood (from a sampling line) and cardiotomy or suction blood (from within the surgical field). Example 1 is a dual chamber blood reservoir including an activated section and a non-activated section. The non-activated, or clean, section includes an elongate filter and a foamer that is disposed about an upper region of the elongate filter. A purgers funnel extends downwardly through the cylindrical foamer and includes a conical upper portion, a cylindrical lower portion and an intervening central portion. A venous inlet tube extends downwardly through the cylindrical lower portion of the purgers funnel to a position that is proximate a bottom surface of the elongate filter. A vent inlet tube extends downwardly through an aperture formed within the central portion of the purgers funnel to a position that is proximate the bottom surface of the elongate filter.

In Example 2, the dual chamber blood reservoir of Example 1 in which blood that exits the cylindrical lower portion of the purgers funnel is able to slide down the exterior surface of the venous inlet tube.

In Example 3, the dual chamber blood reservoir of Example 1 or 2 in which the central portion of the purgers funnel includes a first aperture that is configured to accommodate the vent inlet tube passing therethrough.

In Example 4, the dual chamber blood reservoir of any of Examples 1, 2 or 3, further including a second vent inlet tube that extends downwardly to a position that is proximate the bottom of the elongate filter.

In Example 5, the dual chamber blood reservoir of Example 4, wherein the central portion of the purgers funnel includes a second aperture that is configured to accommodate the second vent inlet tube, the first and second apertures being radially spaced apart about 180 degrees.

In Example 6, the dual chamber blood reservoir of any of Examples 1 to 5, further including a plurality of purge ports that are in fluid communication with the conical upper portion of the purgers funnel.

In Example 7, the dual chamber blood reservoir of any of Examples 1 to 6 in which the activated section includes a suction blood filter assembly including a cylindrical suction blood filter and a defoamer layer that is disposed about the cylindrical suction blood filter.

In Example 8, the dual chamber blood reservoir of any of Examples 1 to 7, further including a releasable barrier between the activated section and the non-activated section, the releasably barrier configured to be released to permit blood within the activated section to enter the non-activated section in a situation requiring additional blood.

In Example 9, the dual chamber blood reservoir of Example 8, further including a porous media disposed to dissipate velocity in blood flowing from the activated section to the non-activated section.

Example 10 is a dual chamber blood reservoir having a housing and a cover spanning the housing. A first vent port and a second vent port each extend through the cover. A venous port extends through the cover. A purgers port extends through the cover. The blood reservoir includes a purgers funnel that has an upper portion, a lower portion and an intervening central portion. The upper portion is in fluid communication with the purgers port. A first vent tube is in fluid communication with the first vent port and extends externally to the lower portion of the purgers funnel to a position near a lower surface of the housing. A second vent tube is in fluid communication with the second vent port and extends externally to the lower portion of the purgers funnel to a position near the lower surface of the housing. A venous tube is in fluid communication with the venous port and extends within the purgers funnel to a position near the lower surface of the housing.

In Example 11, the dual chamber blood reservoir of Example 10 in which the first vent tube extends downwardly within the upper portion of the purgers funnel and passes to an exterior of the purgers funnel through a first aperture formed in the central portion of the purgers funnel.

In Example 12, the dual chamber blood reservoir of Example 10 or 11 in which the first vent tube extends downwardly within the upper portion of the purgers funnel and passes to an exterior of the purgers funnel through a first aperture formed in the central portion of the purgers funnel.

In Example 13, the dual chamber blood reservoir of any of Examples 10 to 12, further including an elongate filter disposed within the housing such that the vent tubes and the venous tube extend downwardly through the elongate filter.

In Example 14, the dual chamber blood reservoir of Example 13 in which the elongate filter has a lower surface that is disposed near the lower surface of the housing.

In Example 15, the dual chamber blood reservoir of any of Examples 10 to 14, further including a plurality of purgers ports that pass through the cover and that are in fluid communication the upper portion of the purgers funnel.

Example 16 is a blood reservoir having a housing and a filtering assembly disposed within the housing. The housing has a top, a bottom, a venous inlet, a vent inlet and a purgers inlet. The filtering assembly extends from near the top of the housing to near the bottom of the housing. The filtering assembly includes a support structure, a filter membrane disposed about the support structure and a defoamer that is disposed about the filter membrane. The filtering assembly includes a purgers funnel that is in fluid communication with the purgers inlet and that extends downwardly within the filter membrane. The filtering assembly includes a venous tube that is in fluid communication with the venous inlet and that extends through an interior of the purgers funnel to a location near a bottom surface of the filtering assembly. The filtering assembly also includes a vent tube that is in fluid communication with the vent inlet and that extends partially through an interior of the purgers funnel and partially exterior to the purgers funnel to a location near the bottom surface of the filtering assembly.

In Example 17, the blood reservoir of Example 16 in which the venous tube and the vent tube extend downwardly within an interior space of the filter membrane.

In Example 18, the blood reservoir of Example 16 or 17 in which the purgers inlet includes a plurality of purgers ports.

Example 19 is an extracorporeal blood circuit that includes a heart lung machine, an oxygenator, a sampling line downstream of the oxygenator and a blood reservoir. The blood reservoir includes a vent blood inlet, a venous blood inlet and a purgers port configured to accept blood from the sampling line. The blood reservoir is configured to accommodate blood from the sampling line without causing excessive gaseous microembolic activity within the blood from the sampling line.

In Example 20, the extracorporeal blood circuit of Example 19 in which the blood reservoir includes a purgers funnel that is in fluid communication with the purgers port, with the venous blood inlet extending downwardly through an interior of the purgers funnel such that blood from the sampling line is permitted to flow downwardly along an exterior surface of the venous blood inlet.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
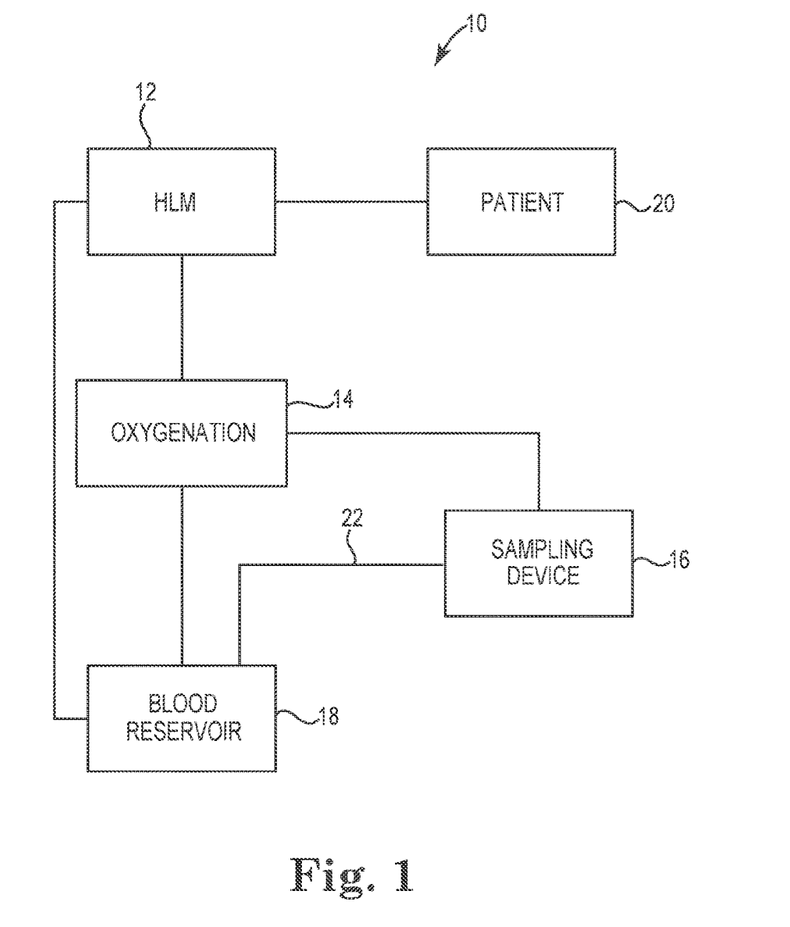
FIG. 1 is a schematic illustration of an extracorporeal blood circuit in accordance with an embodiment of the present invention.

FIG. 1 is a schematic illustration of an extracorporeal blood circuit 10. As illustrated, the extracorporeal blood circuit 10 includes an HLM 12, an oxygenator 14, a sampling device 16 and a blood reservoir 18. The HLM 12 is in fluid communication with a patient 20 and as such can receive blood from the patient 20 and moreover can return blood and other fluids to the patient 20. The sampling device 16 may be a port or similar structure that permits blood to be withdrawn from the extracorporeal blood circuit 10 for lab work and/or additional testing done in the surgical arena. Blood in the sampling device 16 may flow into the blood reservoir 18 through a sampling line 22.

Figure 2:
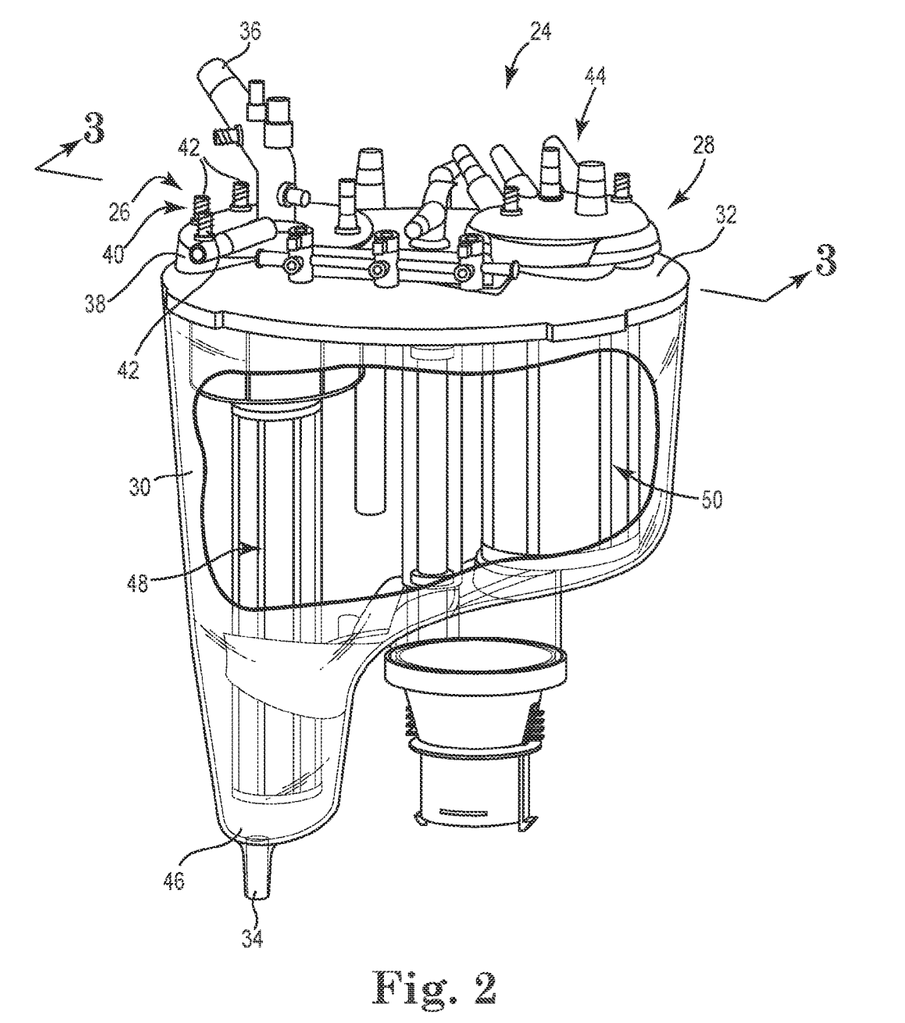
FIG. 2 is a partially cross-sectioned perspective view of a blood reservoir in accordance with an embodiment of the present invention.

FIG. 2 is a partially cross-sectioned perspective view of a blood reservoir 24 that may be used as the blood reservoir 18 in the extracorporeal blood circuit 10 of FIG. 1. The blood reservoir 24 includes a clean (i.e., non-activated) section 26 and a dirty (i.e., activated) section 28. In this, "clean" and "dirty" are relative terms pertaining to an expected level of solid particles or air bubbles within the blood entering each section. For example, vent blood and venous blood, which are usually fairly clean, may be processed within the non-activated section 26, while suction blood, which tends to contain relatively more debris, may be processed within the activated section 28.

As shown in FIG. 2, the blood reservoir 24 includes a housing 30 and a cover 32. A number of blood inlets, as will be described, extend through or are otherwise disposed within the cover 32. The housing 30 includes a blood outlet 34 that may, in some embodiments, be in fluid communication with the HLM 12. The housing 30 tapers to a bottom 46. The cover 32 accommodates a venous inlet port 36, one or more vent inlet ports 38 (only one is visible in this view) and a purgers inlet 40 having one or more purgers ports 42.

The cover 32 also accommodates a suction inlet 44. In some embodiments, one or more of the venous inlet port 36, the vent inlet port(s) 38, the purgers inlet 40 or the suction inlet 44 may pass through the cover 32 such that they can rotate relative to the cover 32.

Figure 3A:
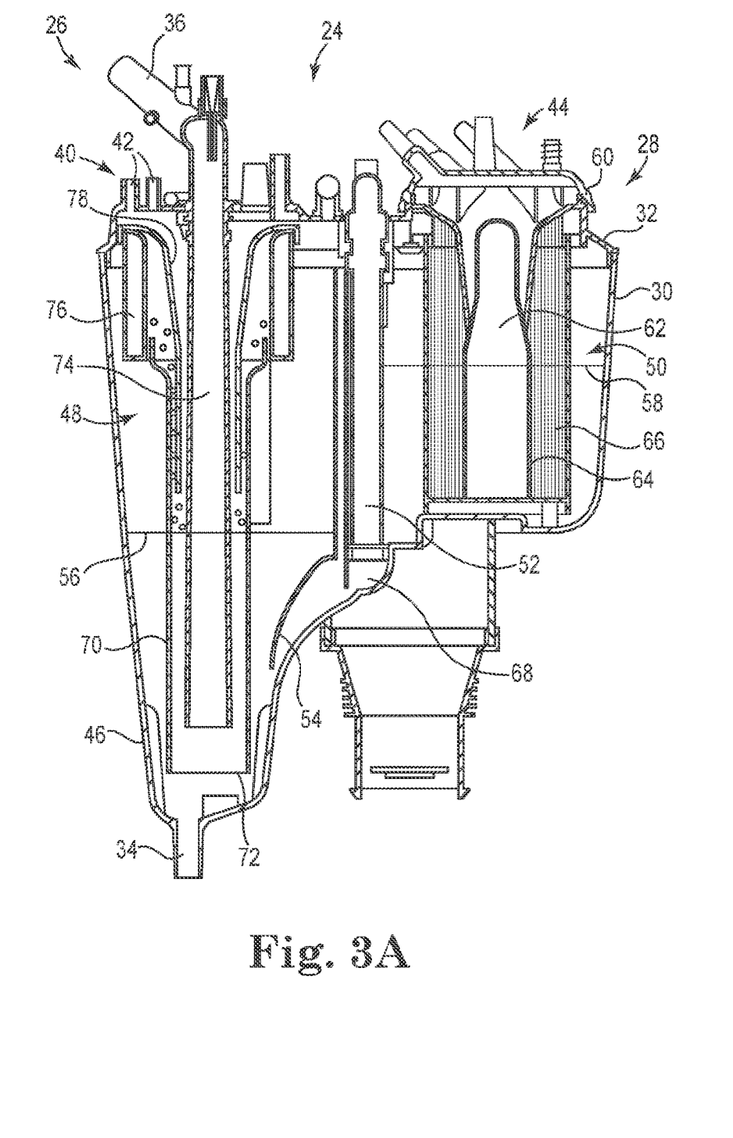
FIG. 3A is a cross-sectional view of the blood reservoir of FIG. 2.

As shown, the non-activated section 26 includes a filtering assembly 48, while the activated section 28 includes a filtering/defoaming assembly 50. FIG. 3A is a cross-sectional view taken along line 3-3 of FIG. 2 and provides greater detail pertaining to the filtering assembly 48 and the filtering/defoaming assembly 50. The blood reservoir 24 includes a movable or releasable valve 52 that, when in place as illustrated, keeps blood within the activated section 28 from entering the non-activated section 26. In some cases, there may be a need for more blood than is available from the non-activated section 26 and thus the valve 52 may be lifted, rotated or otherwise moved to permit blood to pass from the activated section 28 to the non-activated section 26.

In some embodiments, the housing 30 may include a shield 54 that directs blood from the activated section 28 towards the bottom 46. The shield 54 may be shaped and positioned to minimize turbulence within the blood flow. While relative blood levels may vary during use in the non-activated section 26 and the activated section 28 (when the valve 52 is closed), in some embodiments, the blood level within the non-activated section 26, indicated by a line 56, may be relatively lower than the blood level within the activated section 28, as indicated by a line 58. In some embodiments, the blood level within the non-activated section 26 may instead be higher than the blood level within the activated section 28.

In the activated section 28, the suction filtering/defoaming assembly 50 includes several components. Blood from the suction inlet 44 may pass into a collection funnel 60 and may then slide or otherwise flow down a diverter 62 that is configured to minimize turbulence in the blood flow. The blood then passes through a cylindrical filter 64 and a defoamer 66 that is disposed about the cylindrical filter 64. Blood thus filtered then collects within the activated section 28, where it is stored until it is either needed or subsequently discarded through an exit port 68.

In the non-activated section 26, the filtering assembly 48 includes several components, not all of which are visible in FIG. 3A. The filtering assembly 48 includes an elongate cylindrical filter 70 having a lower surface 72. A venous inlet tube 74 that is in fluid communication with the venous inlet port 36 extends downwardly through an interior of the elongate cylindrical filter 70 and terminates at a position that is near the lower surface 72 of the elongate cylindrical filter 70. A cylindrical defoamer 76 is disposed about an upper region of the elongate cylindrical filter 70.

The filtering assembly 48 also includes a purgers funnel 78 that extends downwardly through the cylindrical defoamer 76 and into the elongate cylindrical filter 70. The purgers funnel 78 is in fluid communication with the purgers inlet 40. The venous inlet tube 74 extends downwardly through the purgers funnel 78. In some embodiments, the venous inlet tube 74 has an outer diameter that is less than an inner diameter of the purgers funnel 78 such that purgers blood collected within the purgers funnel 78 may exit the purgers funnel 78 by sliding down an exterior of the venous inlet tube 74. In some embodiments, this reduces turbulence in the flow of purgers blood, thereby reducing or even eliminating the formation of gaseous microembolic activity in the purgers blood. In some embodiments, the purgers funnel 78 may include fingers (not shown) that form an interference fit with the exterior of the venous inlet tube 74 yet permit blood to flow down the exterior of the venous inlet tube 74. In some embodiments, any entrained air within the blood in the non-activated section 26 may travel up into the cylindrical defoamer 76.

Figure 3B:
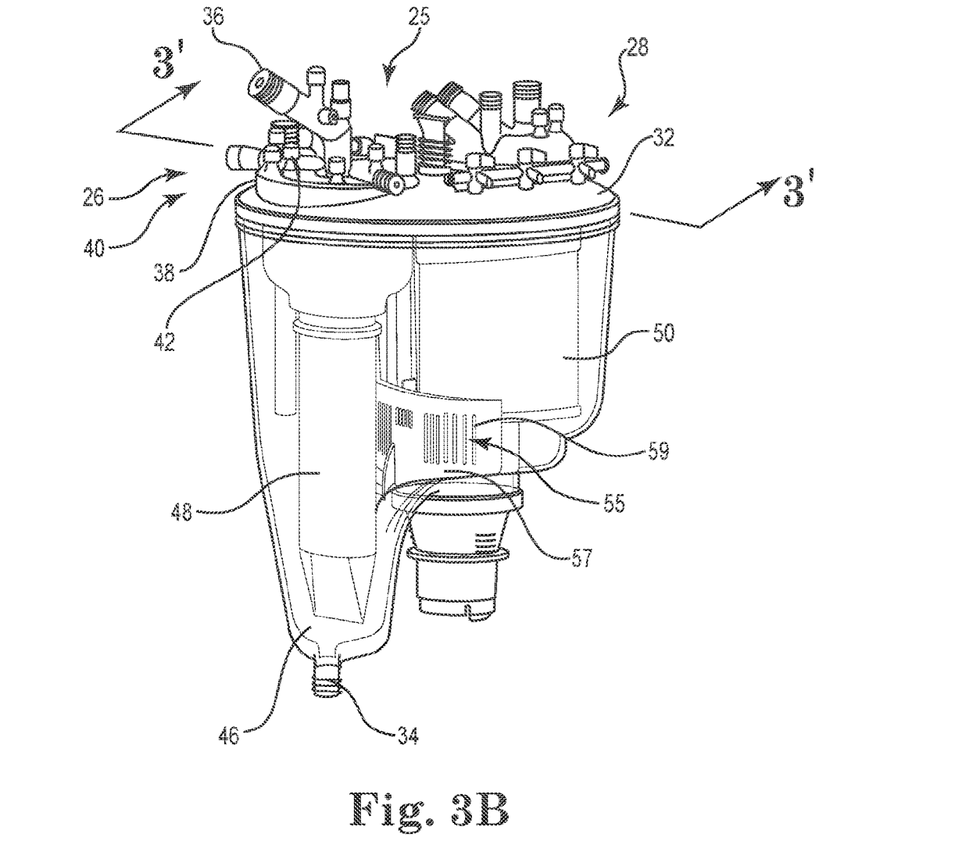
FIG. 3B is a partially cross-sectioned perspective view of a blood reservoir in accordance with an embodiment of the present invention.

FIG. 3B is a partially cross-sectioned perspective view blood reservoir 25 that may be used as the blood reservoir 18 in the extracorporeal blood circuit 10 of FIG. 1. In some embodiments, the blood reservoir 25 is similar in at least some constructional aspects to the blood reservoir 24, and thus similar elements share reference numbers therebetween. The blood reservoir 25 includes a clean (i.e., non-activated) section 26 and a dirty (i.e., activated) section 28. In this, "clean" and "dirty" are relative terms pertaining to an expected level of solid particles or air bubbles within the blood entering each section. For example, vent blood and venous blood, which are usually fairly clean, may be processed within the non-activated section 26, while suction blood, which tends to contain relatively more debris, may be processed within the activated section 28.

As shown in FIG. 3B, the blood reservoir 25 includes a housing 30 and a cover 32. A number of blood inlets, as will be described, extend through or are otherwise disposed within the cover 32. The housing 30 includes a blood outlet 34 that may, in some embodiments, be in fluid communication with the HLM 12. The housing 30 tapers to a bottom 46. The cover 32 accommodates a venous inlet port 36, one or more vent inlet ports 38 (only one is visible in this view) and a purgers inlet 40 having one or more purgers ports 42. The cover 32 also accommodates a suction inlet 44. In some embodiments, one or more of the venous inlet port 36, the vent inlet port(s) 38, the purgers inlet 40 or the suction inlet 44 may pass through the cover 32 such that they can rotate relative to the cover 32. As shown, the non-activated section 26 includes a filtering assembly 48, while the activated section 28 includes a filtering/defoaming assembly 50.

Figure 3C:
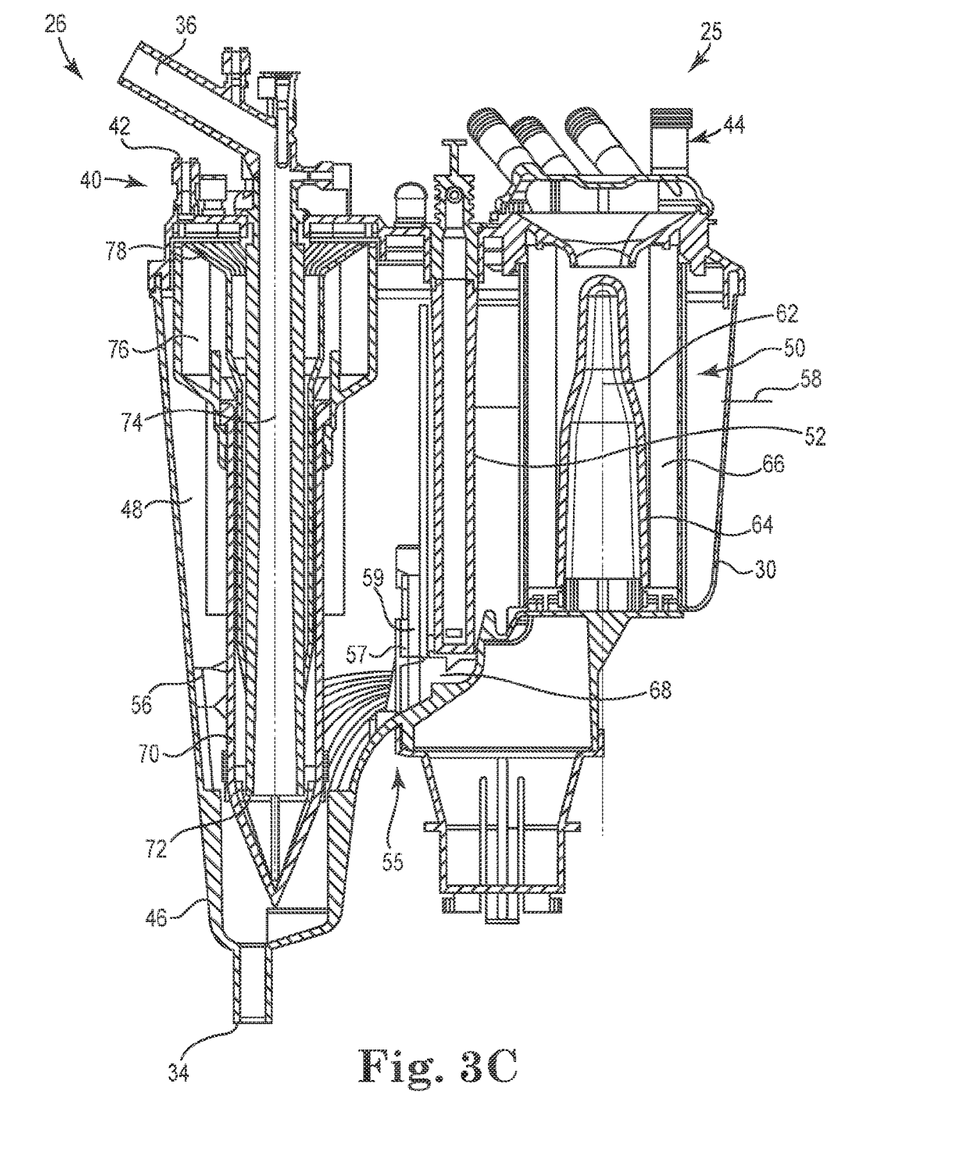
FIG. 3C is a cross-sectional view of the blood reservoir of FIG. 3B.

FIG. 3C is a cross-sectional view taken along line 3'-3' of FIG. 3B and provides greater detail pertaining to the filtering assembly 48 and the filtering/defoaming assembly 50. The blood reservoir 25 includes a movable or releasable valve 52 that, when in place as illustrated, keeps blood within the activated section 28 from entering the non-activated section 26. In some cases, there may be a need for more blood than is available from the non-activated section 26 and thus the valve 52 may be lifted, rotated or otherwise moved to permit blood to pass from the activated section 28 to the non-activated section 26.

In some embodiments, the housing 30 may include a shield 55 that directs blood from the activated section 28 towards the bottom 46. The shield 55 may be shaped and positioned to minimize turbulence within the blood flow. In some embodiments, as illustrated, the shield 55 may include a frame portion 57 and a porous media portion 59. The frame portion 57 supports the porous media portion 59 and helps to anchor the shield 55 within the housing 30. The porous media portion 59 slows blood passing through the shield 55.

While relative blood levels may vary during use in the non-activated section 26 and the activated section 28 (when the barrier 52 is closed), in some embodiments, the blood level within the non-activated section 26, indicated by a line 56, may be relatively lower than the blood level within the activated section 28, as indicated by a line 58. In some embodiments, the blood level within the non-activated section 26 may instead be higher than the blood level within the activated section 28.

In the activated section 28, the suction filtering/defoaming assembly 50 includes several components. Blood from the suction inlet 44 may pass into a collection funnel 60 and may then slide or otherwise flow down a diverter 62 that is configured to minimize turbulence in the blood flow. The blood then passes through a cylindrical filter 64 and a defoamer 66 that is disposed about the cylindrical filter 64. Blood thus filtered then collects within the activated section 28, where it is stored until it is either needed or subsequently discarded through an exit port 68. In some embodiments, blood stored within the activated section 28 may be released into the non-activated section 26 by opening the valve 52.

In the non-activated section 26, the filtering assembly 48 includes several components, not all of which are visible in FIG. 3A. The filtering assembly 48 includes an elongate cylindrical filter 70 having a lower surface 72. A venous inlet tube 74 that is in fluid communication with the venous inlet port 36 extends downwardly through an interior of the elongate cylindrical filter 70 and terminates at a position that is near the lower surface 72 of the elongate cylindrical filter 70. A cylindrical defoamer 76 is disposed about an upper region of the elongate cylindrical filter 70.

The filtering assembly 48 also includes a purgers funnel 78 that extends downwardly through the cylindrical defoamer 76 and into the elongate cylindrical filter 70. The purgers funnel 78 is in fluid communication with the purgers inlet 40. The venous inlet tube 74 extends downwardly through the purgers funnel 78. In some embodiments, the venous inlet tube 74 has an outer diameter that is less than an inner diameter of the purgers funnel 78 such that purgers blood collected within the purgers funnel 78 may exit the purgers funnel 78 by sliding down an exterior of the venous inlet tube 74. In some embodiments, this reduces turbulence in the flow of purgers blood, thereby reducing or even eliminating the formation of gaseous microembolic activity in the purgers blood. In some embodiments, the purgers funnel 78 may include fingers (not shown) that form an interference fit with the exterior of the venous inlet tube 74 yet permit blood to flow down the exterior of the venous inlet tube 74. In some embodiments, any entrained air within the blood in the non-activated section 26 may travel up into the cylindrical defoamer 76.

Figure 4:
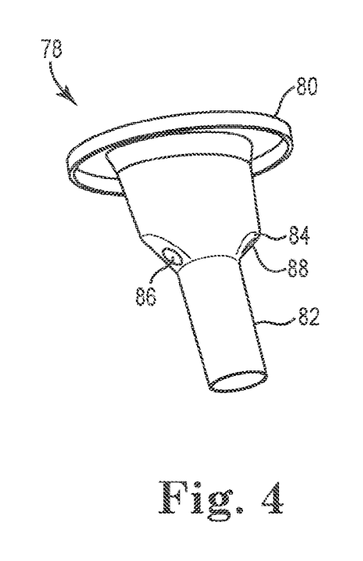
FIG. 4 is a perspective view of a purgers funnel in accordance with an embodiment of the present invention.

FIG. 4 is a perspective view of an embodiment of the purgers funnel 78. In the illustrated embodiment, the purgers funnel 78 includes an upper portion 80, a lower portion 82 and a tapered central portion 84 between the upper portion 80 and the lower portion 82. In some embodiments, the upper portion 80 may be conical or otherwise tapered in shape. In some cases, the lower portion 82 may be cylindrical in shape. In the illustrated embodiment, the central portion 84 of the purgers funnel 78 includes a first aperture 86 and a second aperture 88. The first aperture 86 and the second aperture 88 may be configured to permit first and second vent tubes (illustrated in a subsequent Figure) to pass therethrough. In some embodiments, the first aperture 86 and the second aperture 88 may be radially spaced about 180 degrees apart.

Figure 5:
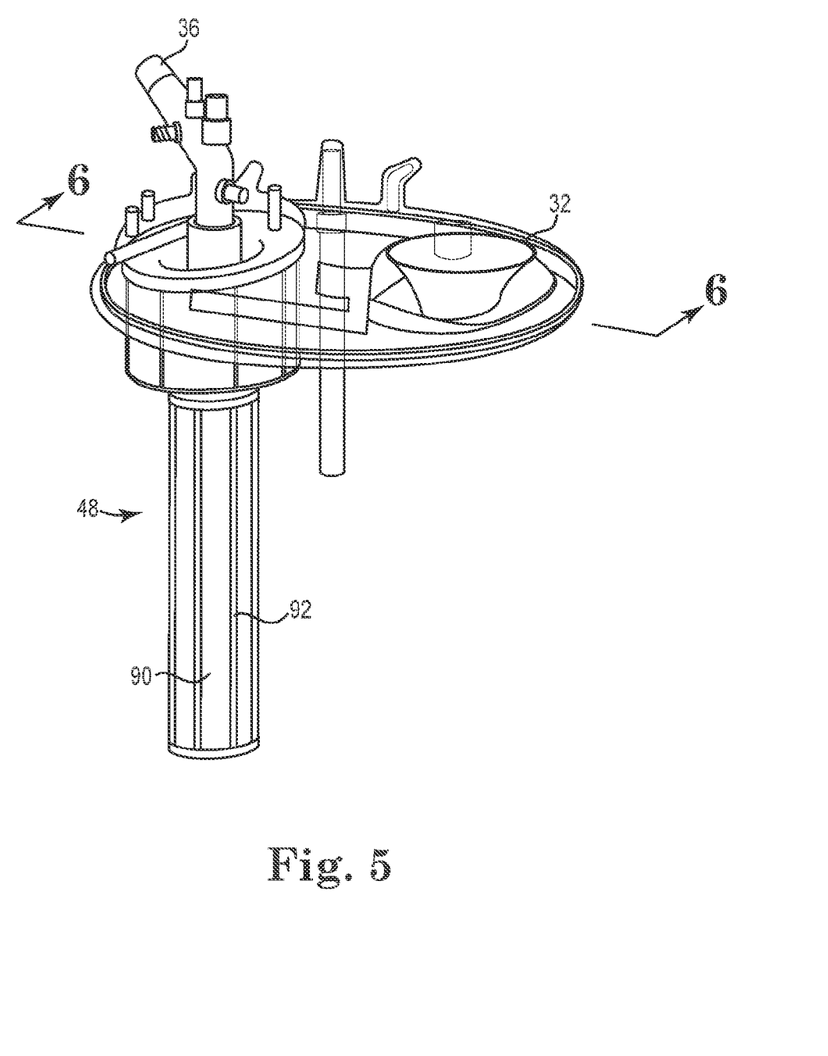
FIG. 5 is a perspective view of a filtering assembly in accordance with an embodiment of the present invention.

FIG. 5 is a perspective view of the filtering assembly 48. The filtering assembly 48 includes, as shown in FIG. 3A, the elongate cylindrical filter 70 and the cylindrical defoamer 76. The elongate cylindrical filter 70 includes a filter membrane 90 and a support structure 92. As illustrated, the filter membrane 90 is disposed inside of the support structure 92. In some embodiments, the filter membrane 90 may instead be disposed about the support structure 92. The support structure 92 may provide sufficient support to the filter membrane 90 to hold the filter membrane 90 in a desired configuration against the fluid pressures to which the filter membrane 90 may be exposed during operation of the blood reservoir 24.

Figure 6:
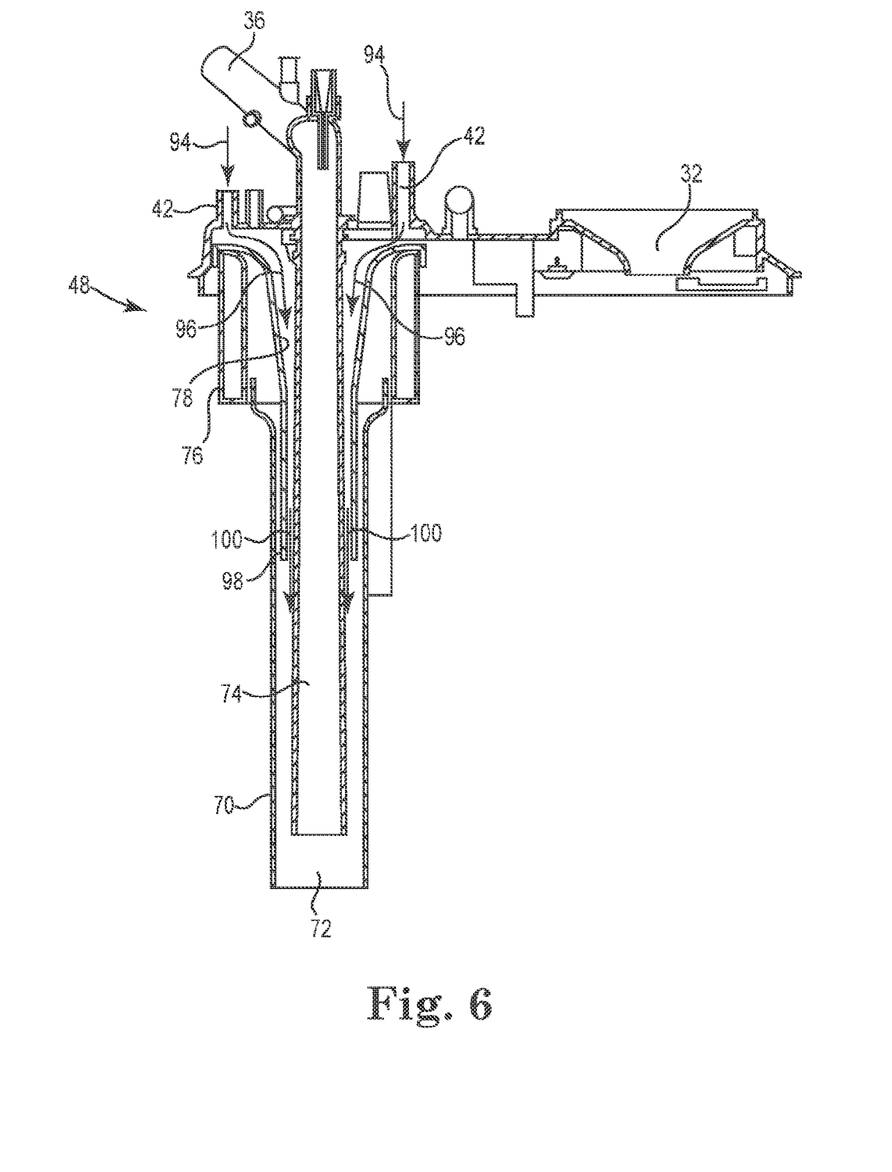
FIG. 6 is a cross-sectional view of the filtering assembly of FIG. 5.

FIG. 6 is a cross-sectional view taken along line 6-6 of FIG. 5 and illustrates a blood flow path for purgers blood. As indicated by arrows 94, purge blood may enter the blood reservoir 24 through the purgers ports 42. The purgers blood then travels down through the purgers funnel 78 as indicated by arrows 96, and exits through a bottom 98 of the purgers funnel 78. As indicated by arrows 100, the blood then slides or otherwise flows down the exterior surface of the venous inlet tube 74.

Figure 7:
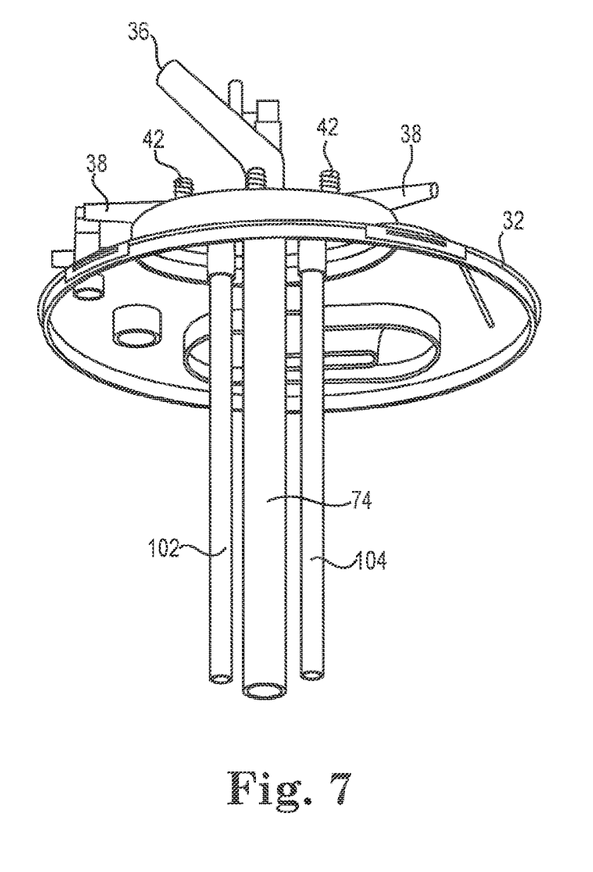
FIG. 7 is a perspective view of a portion of the filtering assembly of FIG. 5.

FIG. 7 is a perspective view of a portion of the filtering assembly 48, illustrating the venous inlet tube 74, a first vent tube 102 and a second vent tube 104. The venous inlet tube 74, the first vent tube 102 and the second vent tube 104 extend downwardly from the cover 32 through an interior of the elongate cylindrical filter 70. As shown in FIG. 4, the first vent tube 102 may pass through the first aperture 86 and the second vent tube 104 may pass through the second aperture 88. The first vent tube 102 may be considered as extending within the purgers funnel 78 above the first aperture 86 but exterior to the purgers funnel 78 below the first aperture 86. Similarly, the second vent tube 104 may be considered as extending within the purgers funnel 78 above the second aperture 88 but exterior to the purgers funnel 78 below the second aperture 88. In some embodiments, the venous inlet tube 74, the first vent tube 102 and the second vent tube 104 each extend downwardly to a position that is proximate or near to the lower surface 72 of the elongate cylindrical filter 70. As a result, in some embodiments, turbulence and resulting blood cell damage may be reduced or eliminated.

Figure 8:
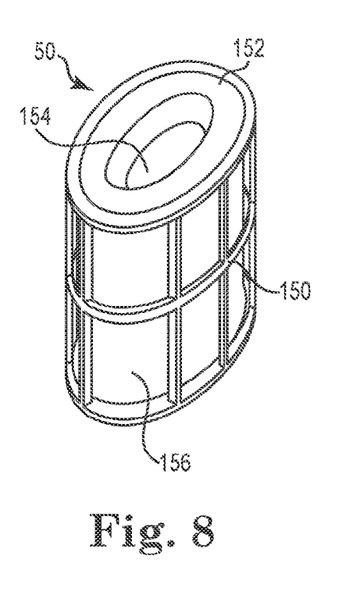
FIG. 8 is a perspective view of a filtering assembly in accordance with an embodiment of the present invention.

FIG. 8 is a perspective view of an embodiment of the filtering/defoaming assembly 50. In some embodiments, the filtering/defoaming assembly 50 includes a plastic frame 150 that supports the filtering/defoaming assembly 50 and provides the filtering/defoaming assembly 50 with an annular or ovoid shape. A foam cylinder such as a polyurethane foam cylinder 152 is disposed within the plastic frame 150 and at least partially defines an internal sliding surface 154. An outer surface of the foam cylinder 152 is at least partially wrapped in a polyester felt 156. In some embodiments, the polyester felt 156 has a pore size of about 40 microns.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A blood reservoir for use with a heart lung machine, the blood reservoir comprising:
   a housing including a venous blood inlet,
   a purgers port for accepting blood from a sampling line,
   a purgers funnel in fluid communication with the purgers port, and
   a defoamer disposed such that the purgers funnel extends through the defoamer and at least part of the purgers funnel extends below the defoamer,
   wherein the venous blood inlet extends downwardly through an interior of the purgers funnel, the purgers funnel being configured to permit the blood from the sampling line to exit the purgers funnel and flow downwardly along an exterior surface of the venous blood inlet.

2. The blood reservoir of claim 1, wherein the purgers funnel has an upper portion, a lower portion and a central portion, wherein the upper portion of the purgers funnel is in fluid communication with the purgers port.

3. The blood reservoir of claim 2, further comprising:
a venous tube in fluid communication with the venous blood inlet and extending within the purgers funnel, such that the lower portion of the purgers funnel is configured to extend alongside a portion of the venous tube.

4. The blood reservoir of claim 3, wherein the lower portion of the purgers funnel has an inner diameter that is greater than an outer diameter of the venous tube such that blood exiting the purgers funnel slides down an exterior surface of the venous tube.

5. The blood reservoir of claim 4, further comprising:
an elongate filter disposed such that the venous tube extends downwardly inside the elongate filter.

6. The blood reservoir of claim 5, wherein the elongate filter extends to near a lower surface of the housing.

7. The blood reservoir of claim 6, wherein the elongate filter extends beyond a lower end of the venous tube.

8. The blood reservoir of claim 2, further comprising:
a first vent blood inlet, and
a first vent tube in fluid communication with the first vent blood inlet and extending external to the lower portion of the purgers funnel,
wherein the first vent tube extends downwardly within the upper portion of the purgers funnel and passes to an exterior thereof through a first aperture formed in the central portion of the purgers funnel.

9. The blood reservoir of claim 8, further comprising:
a second vent blood inlet, and
a second vent tube in fluid communication with the second vent blood inlet and extending external to the lower portion of the purgers funnel,
wherein the second vent tube extends downwardly within the upper portion of the purgers funnel and passes to an exterior thereof through a second aperture formed in the central portion of the purgers funnel.

10. A blood reservoir for use with a heart lung machine, the blood reservoir comprising:
a housing including a purgers port for accepting blood from a sampling line,
a purgers funnel, and
a defoamer,
wherein the purgers funnel includes an upper portion, a lower portion and a central portion, the upper portion in fluid communication with the purgers port,
wherein the defoamer is positioned so the purgers funnel extends through the defoamer and at least part of the lower portion of the purgers funnel extends below the defoamer.

11. The blood reservoir of claim 10, further comprising:
a venous blood inlet tube extending downwardly through an interior of the purgers funnel,
wherein the purgers funnel is configured to permit the blood from the sampling line to flow downwardly along an exterior surface of the venous blood inlet tube.

12. The blood reservoir of claim 11, wherein the venous blood inlet tube extends downwardly within the upper portion of the purgers funnel and passes to an exterior thereof through a first aperture formed in the central portion of the purgers funnel.

13. The blood reservoir of claim 12, further comprising:
an elongate filter disposed around at least the lower portion of the purgers funnel.

14. The blood reservoir of claim 13, wherein the elongate filter extends to near a lower surface of the housing.

15. The blood reservoir of claim 14, wherein the elongate filter extends beyond a lower end of the venous blood inlet tube.

16. The blood reservoir of claim 10, further comprising:
a shield,
wherein the blood reservoir includes an activated section and a non-activated section, and the shield is situated between the activated section and the non-activated section and configured to direct blood from the activated section to the non-activated section.

17. The blood reservoir of claim 16, wherein the shield includes a frame and a porous media disposed within the frame to dissipate velocity of blood flowing from the activated section to the non-activated section.

18. The blood reservoir of claim 16, further comprising:
a releasable valve configured to keep blood within the activated section from entering the non-activated section until the valve is released.

19. The blood reservoir of claim 16, wherein the activated section includes a filtering and defoaming assembly.

* * * * *